United States Patent [19]
Uematsu et al.

[11] Patent Number: 6,146,882
[45] Date of Patent: Nov. 14, 2000

[54] INCUBATOR AND ANALYZER INCLUDING SUCH INCUBATOR

[75] Inventors: Hiroaki Uematsu; Takashi Nakajima, both of Shiga; Tatsuo Arai; Keiji Okumoto, both of Hyogo, all of Japan

[73] Assignees: Toyo Boseki Kabushiki Kaisha, Osaka; Furuno Electric Co, Ltd., Hyogo, both of Japan

[21] Appl. No.: 09/242,448

[22] PCT Filed: Jun. 15, 1998

[86] PCT No.: PCT/JP98/02658

§ 371 Date: Mar. 30, 1999

§ 102(e) Date: Mar. 30, 1999

[30] Foreign Application Priority Data

Jun. 20, 1997 [JP] Japan ................................. 9-163724

[51] Int. Cl.[7] ..................................................... C12M 1/34
[52] U.S. Cl. .................................. 435/303.1; 435/286.2; 435/287.2; 435/287.3; 435/288.7; 422/65; 422/82.05
[58] Field of Search ............................. 422/63, 65, 82.05; 435/286.2, 286.4, 287.2, 287.3, 288.7, 303.1

[56] References Cited

U.S. PATENT DOCUMENTS 5,779,981   7/1998   Danssaert et al. ........................ 422/99

FOREIGN PATENT DOCUMENTS 2176910   7/1990   Japan .
5168459   7/1993   Japan .
6277036   10/1994  Japan .
6308133   11/1994  Japan .

*Primary Examiner*—David A. Redding

[57] ABSTRACT

An incubator comprises an incubating block (12) for incubating a sample at an any desired processing temperature by storing a well rack (14) held the sample such as specimens for instance, under that temperature, a cooling block (13) set to a cooling temperature, a dummy rack (15) which are cooled in the cooling block (13) during an incubating process, as well as first and second pushers (18a, 18b) and first and second carriages (19a, 19b) which together exchange the well rack (14) and the dummy rack (15) with each other.

9 Claims, 8 Drawing Sheets

INCUBATOR AND ANALYZER INCLUDING SUCH INCUBATOR

This application is the national phase under 35 U.S.C. §371 of prior PCT International Application No. PCT/JP98/02658 which has an International filing date of Jun. 15, 1998 which designated the United States of America.

TECHNICAL FIELD

The present invention relates to an incubator capable of maintaining a sample at any desired processing temperature and an analyzer including such incubator.

BACKGROUND ART

Generally, Nucleic acid automation analyzers and blood analyzers are equipped with an incubator capable of maintaining samples, such as blood or DNA taken from specimens, at any desired processing temperature as it is necessary for these analyzers to perform various kinds of processing on the samples at optimum processing temperatures before analyzing the samples.

A conventional incubator is constructed such that a storage block which can accommodate reaction vessels loaded with samples is fitted with a thermo-module, by which the storage block is heated or cooled in accordance with specified processing temperatures. In this type of construction, in which the whole of one storage block is heated and cooled, a long period of time is required for controlling it from one processing temperature to another, causing a significantly long waiting time, if there is a large temperature difference between successive processing steps. A proposal made in a recent year (Japanese Unexamined Patent Publication No. HEI 6-277036) discloses a construction as shown in FIG. 9, in which a cooling block 53 cooled by a cooling fan 51 and a radiator plate 52 and a heating block 55 heated by a heater 54 are individually preset to their cooling and processing temperatures, respectively, and reaction cuvettes 56 are moved back and forth between the two blocks 55, 53 to thereby reduce the waiting time required for temperature control.

There exists a problem in such conventional construction simply incorporating the cooling block 53 and the heating block 55, however, that it is difficult to control the temperature following any desired processing temperature settings at a high speed. This is because the temperature in the heating block 55 is controlled by a heating process performed by the heater 54 and a heat dissipation process.

More specifically, it would be possible to achieve an increased rate of temperature rise in the heating block 55 by adopting measures such as increasing a capacity of the heater 54, reducing a capacity of the reaction cuvettes 56, or a greater heat insulating ability, for example. It is however difficult in actuality to take measures such as reducing the capacity of the reaction cuvettes 56 or the increasing the capacity of the heater 54, since an analyzer to be equipped with the incubator is restricted in its specifications. On the other hand, the greater heat insulating ability is extremely important in ensuring the stability of temperature required for the incubator. Therefore, the increase in the rate of temperature rise in the heating block 55 is usually realized by taking measures which are mainly focused on the heat insulating ability and yet permit increased stability of temperature.

If, however, the heating block 55 is so constructed as to achieve great ability of heat insulating, the rate of heat dissipation during a process of temperature drop, which occurs after stopping the heating process by the heater 54, decreases and, as a consequence, the process of temperature drop slows down. For reasons stated above, it has been necessary to sacrifice at least one of the temperature rise efficiency and the temperature drop efficiency in the conventional incubator and, therefore, it has been difficult to control the temperature following any processing temperature settings at a high speed.

Accordingly, it is an object of the invention to provide an incubator which permits high-speed temperature control, swiftly following arbitrarily any processing temperature settings, by increasing both the rate of temperature rise and the rate of temperature drop as well as an analyzer equipped with such incubator.

SUMMARY OF THE INVENTION

According to the invention, an incubator comprises a vessel for holding a sample, a well rack for accommodating said vessel, incubation means for incubating said sample at an any desired processing temperature by storing said well rack under that temperature, cooling means set to a cooling temperature, a dummy rack being cooled by said cooling means during said sample is incubated, and exchange means for exchanging said well rack and said dummy rack with each other between said incubation means and said cooling means.

In this construction, when the dummy rack cooled by the cooling means is exchanged with the well rack, the incubation means is forcibly cooled by the dummy rack. Thus, a high rate of temperature drop of the incubation means is obtained even when the rate of heat dissipation of the incubation means is decreased to expedite its temperature rise. Since both the rate of temperature rise and the rate of temperature drop can be increased, it is possible to achieve high-speed temperature control capable of swiftly following arbitrarily any processing temperature settings.

Furthermore, since incubating operation and cooling operation for the sample in the well rack can be performed independently in the incubation means and in the cooling means respectively, it is possible to design these means in such a way that the incubation means has a structure suited for the incubating operation and the cooling means has a structure suited for the cooling operation. Accordingly, overall design work becomes easier than designing a structure suited for both of the incubating and cooling operations.

Furthermore, since the dummy rack is cooled by the cooling means while the well rack is incubated by the incubation means, and the well rack is cooled by the cooling means while the incubation means is cooled by the dummy rack, it is possible to efficiently perform the incubating and cooling operations without requiring such meaningless operations as temporarily moving the dummy rack or the well rack to locations other than the incubation means and the cooling means.

According to the invention, an incubator comprises a vessel for holding a sample, a plurality of well racks for accommodating said vessel, being arranged parallel to one another, incubation means for incubating said sample at an any desired processing temperature by storing said well racks under that temperature, cooling means set to a cooling temperature, a plurality of dummy racks being cooled by said cooling means during the sample is incubated, being arranged parallel to one another and, injection means, settled at an injecting position set between said incubation means and said cooling means, for injecting the sample into said well of said well racks passing the injecting position, and exchange means for exchanging said well racks and said dummy racks with one another between said incubation means and said cooling means by transporting said well racks and said dummy racks through the injecting position.

This construction makes it possible to efficiently incubate and cool the multiple well racks. Furthermore, it is possible to efficiently perform sample injecting operation for the individual well racks as the sample can be injected into each well of the well racks by the injection means on its way from the cooling means to the incubation means.

The incubation means of the invention includes a cooling fan which is operated when lowering the processing temperature. This makes it possible to further increase the rate of temperature drop of the incubation means.

The cooling means of the invention includes cooling acceleration means for accelerating the cooling operation. This construction makes it possible to instantly cool the dummy racks when the dummy racks which have been heated by the incubation means are returned to the cooling means.

In this invention, there is formed a groove rack in each dummy, for accelerating heat dissipation by increase of its surface area. As the increased surface area accelerates heat dissipation in this construction, it is possible to promptly cool the individual dummy racks.

The incubation means and the cooling means of the invention individually store more than one of the well racks and the dummy racks parallel to one another in such a way that they can be moved in one direction, the incubation means and the cooling means being arranged parallel to each other, wherein the exchange means includes a first pusher provided at one end of the incubation means, the first pusher being capable of pushing out any one of the well racks and the dummy racks stored in the incubation means to its other end, a second pusher provided at one end of the cooling means, opposite to the end of the incubation means where the first pusher is provided, the second pusher being capable of pushing out any one of the well racks and the dummy racks stored in the cooling means to its other end, and carriages provided at both ends of the incubation means and the cooling means in such a way that the carriages can move in a direction along which the incubation means and the cooling means are arranged, the carriages being capable of holding any one of the well racks and the dummy racks pushed out by the first pusher and the second pusher.

Since the exchange means is constructed of such simple mechanical components as the first and second pushers and the carriages, it is possible to reduce component costs of the incubator as well as manufacturing costs incurred in its assembly operation.

According to the invention, an analyzer comprises a plurality of incubators having the aforementioned constructions and examination means for examining samples of the well racks stored in any one of the incubators, wherein the examination means is shared by the incubators.

As the examination means, whose cost tends to increase dramatically due to a move toward higher accuracy of analysis, is shared by the multiple incubators in this construction, it is possible to reduce the component costs compared to a case in which the examination means is separately provided for each individual incubator.

The analyzer is further equipped with transport means which can move to a any desired position over the incubators so that it can carry the samples to and from the well racks, and the examination means is attached to the transport means.

Since the examination means can be moved to and set in a any desired position over the incubators by the transport means in this construction, the examination means can always be shared by the multiple incubators regardless of the direction in which the incubators are arranged or the number of the incubators. Accordingly, it becomes possible to increase the degree of freedom in designing an analyzer with respect to its technical specifications, such as equipment layout and the scale of examination. As the transport means for moving the examination means is originally intended for carrying the samples to and from the well racks, this construction does not entail an increase in component costs as would be incurred when a dedicated mechanism for moving the examination means is provided.

The analyzer of the invention comprises a pair of incubators having the aforementioned constructions and examination means for examining samples of the well racks stored in either of the incubators, wherein the examination means is located on a path along which each of the carriages travels between the incubators.

Since each well rack can be moved by exchange means up to the location of the examination means and subjected to an examination in this construction, it is possible to achieve a further reduction in component costs.

BEST MODE OF CARRYING OUT THE INVENTION

A mode of carrying out the invention, or an embodiment thereof, is described below with reference to FIGS. 1 through 8.

Figure 3:
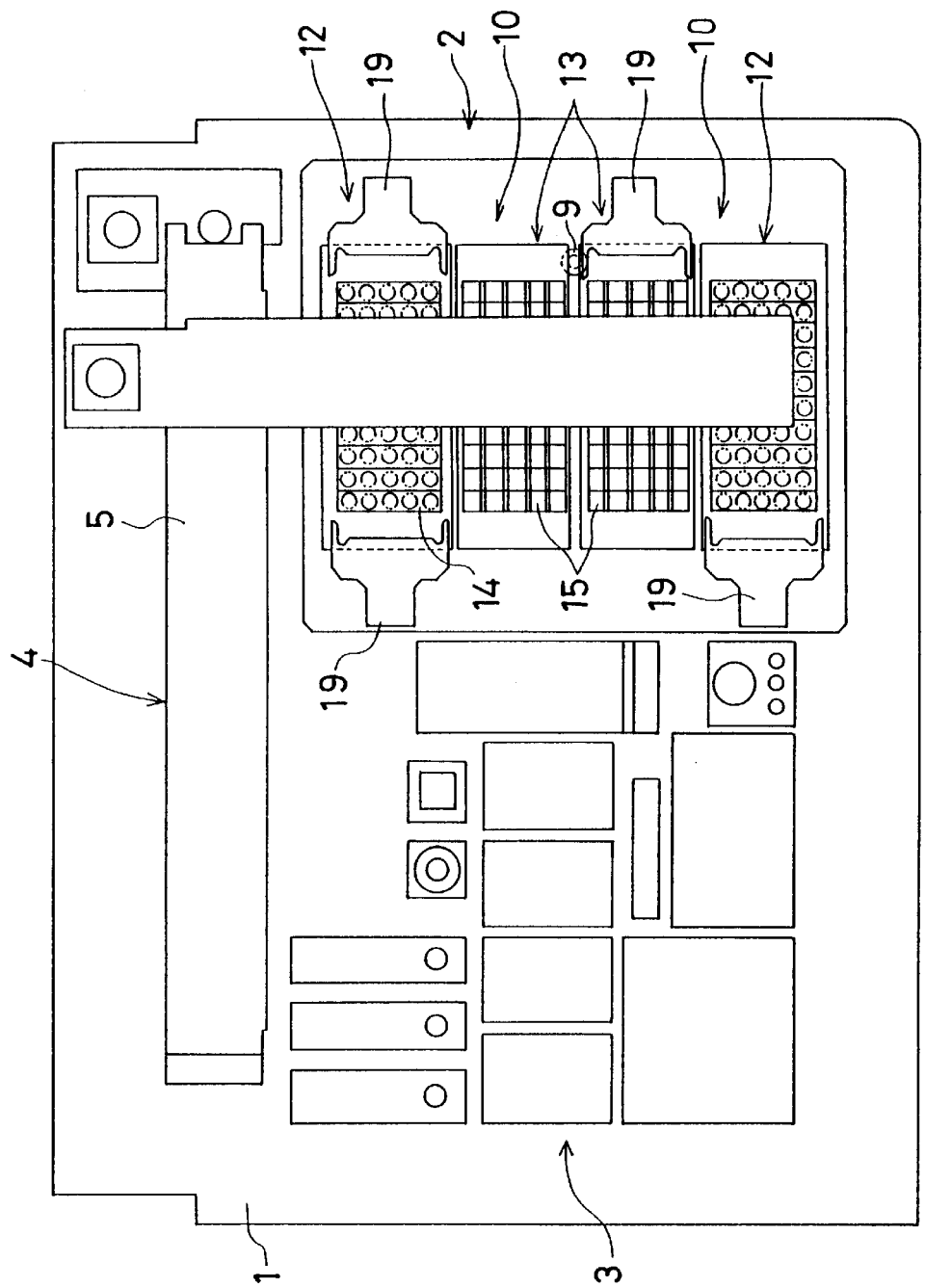
FIG. 3 is a general plan view of an analyzer.

Incubators according to the embodiment are installed in an analyzer for analyzing nucleic acids or blood as shown in FIG. 3. This analyzer comprises a table 1 which is divided into an analysis processing section 2, a storage section 3 and a transport section 4. There are provided shelves for injection tips, specimens, standard solutions, wells, etc. and a storage compartment for storing bottles holding various solutions, such as washing liquids and reagents, in the storage section 3. A transport arm 5 capable of moving in three-dimensional directions is provided in the transport section 4. The transport arm 5 is used for conveying the reagents and specimens of body material between the storage section 3 and the analysis processing section 2.

Figure 7:
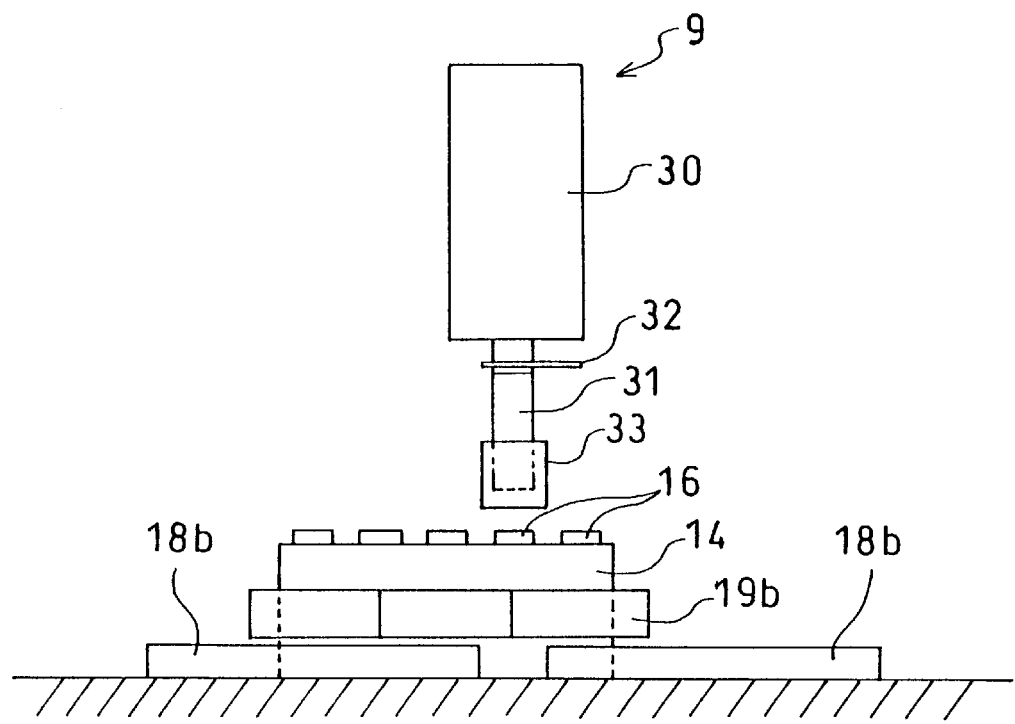
FIG. 7 is a front view of an optical measuring unit and its nearby elements.

In the aforementioned analysis processing section 2, there are provided an optical measuring unit 9 and a pair of incubators 10. As shown in FIG. 7, the optical measuring unit 9 includes a photomultiplier module 30 which produces an output signal according to the amount of incident light, an optical guide tube 31 for guiding the light to the photomultiplier module 30, a shutter plate 32 which is settled midway in the extension of the optical guide tube 31 and is capable of opening and closing its optical path to selectively admit or shut off the incident light, and a light-shielding hood 33 which is movably attached up and down at a lower end portion of the optical guide tube 31 so that the light-shielding hood 33 can cover each of later-described well 16 (vessel) to create a darkroom environment.

Figure 1:
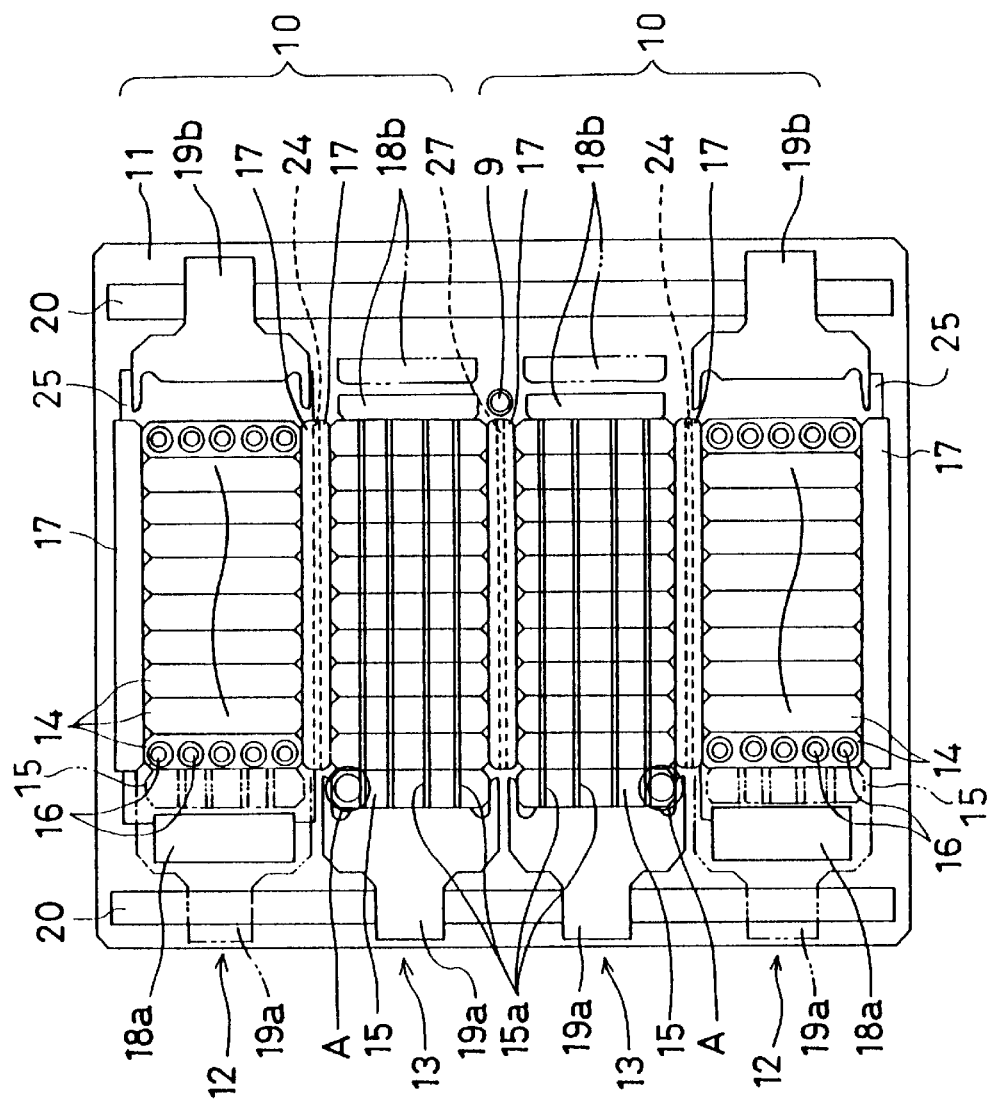
FIG. 1 is a plan view of incubators.

On the other hand, the pair of incubators 10 are mounted on a flat plate-like support base 11 as shown in FIG. 1. Each of the incubators 10 includes an incubating block 12 which is set to a high-temperature condition, is constructed as to decrease the rate of heat dissipation, and a cooling block 13 which is set to a low-temperature condition. The incubating blocks 12 and the cooling blocks 13 of the two incubators 10 being arranged symmetrically on both sides of the optical measuring unit 9. Each incubator 10 is equipped with a vibration table 25 which can be moved to the left and right or to the front and back. The vibration table 25 is constructed such that its portion for each of later-described well racks 14 can be individually oscillated to agitate samples such as specimens or reagents for instance, while they are incubated.

Figure 4:
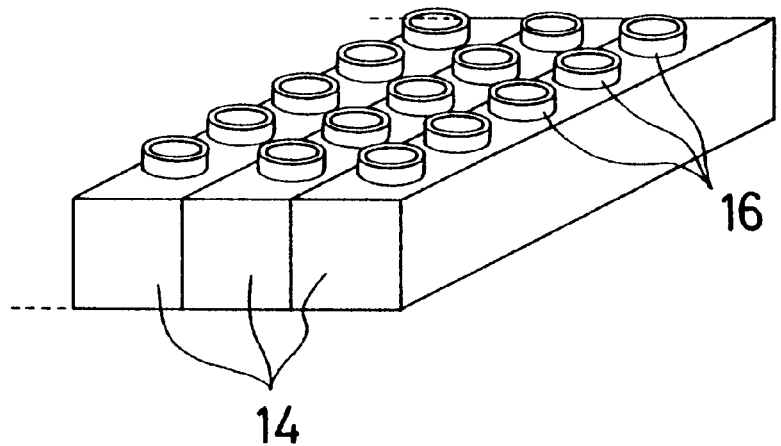
FIG. 4 is a perspective view of well racks.
Figure 5:
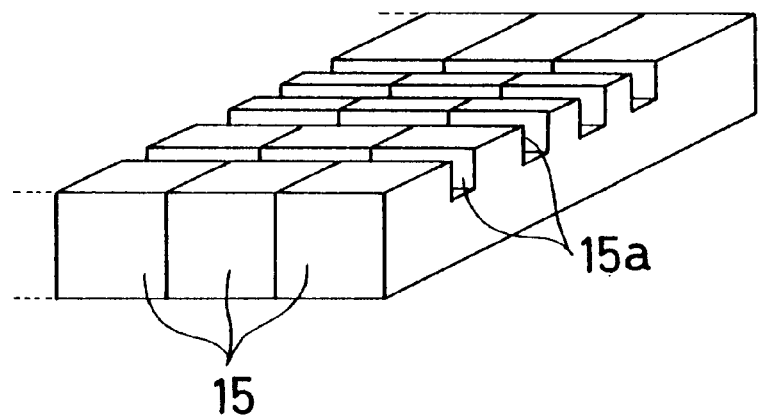
FIG. 5 is a perspective view of dummy racks.
Figure 6:
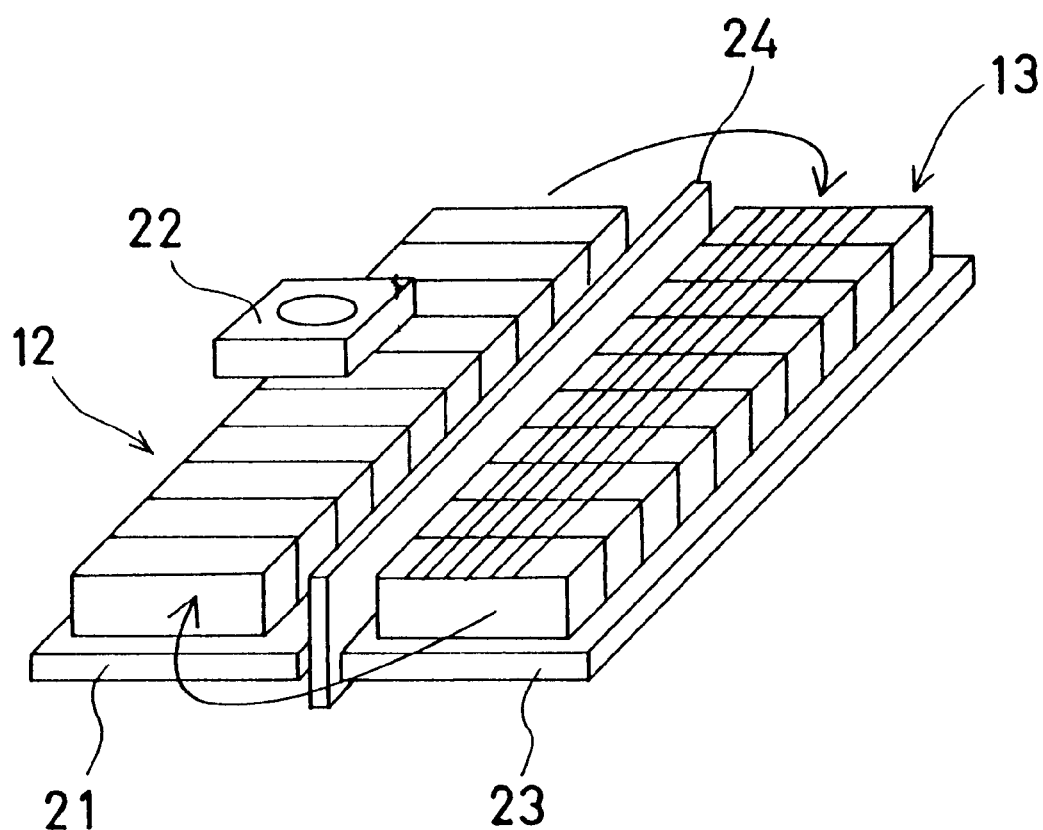
FIG. 6 is an explanatory diagram showing how the well racks and the dummy racks are replaced with one another.

A plurality of well racks 14 and dummy racks 15 are movably placed in each of the incubating blocks 12 and the cooling blocks 13. The individual well racks 14 removably accommodate a plurality of wells 16 which can hold specimens of body material or reagents for instance, as shown in FIG. 4. On the other hand, the dummy racks 15 each have a plurality of grooves 15a in their upper surfaces as shown in FIG. 5 so that the amount of heat dissipation per unit time is increased as a result of an increase in surface area.

The aforementioned well racks 14 and dummy racks 15 are each formed into an elongate boxlike shape of a common size and arranged side by side with their side surfaces held in mutual contact as depicted in FIG. 1. The incubating blocks 12 and the cooling blocks 13 accommodating the racks 14, 15 are separated from one another by guide members 17 which are fitted parallel to the direction in which the individual racks 14, 15 are arranged. The guide members 17 are disposed such that their intervals can be increased and decreased. The intervals between them are increased to permit the racks 14, 15 to move freely when they should be moved, whereas the intervals are decreased to hold the racks 14, 15 in position when they should be vibrated.

There are provided rail members 20 at both ends of each of the incubating blocks 12 and the cooling blocks 13, each rail member 20 alternately passing along the successive blocks 12, 13. Each of these rail members 20 is movably provided with first and second carriages 19a, 19b for holding the racks 14, 15. The racks 14, 15 can be moved between one of the incubating blocks 12 and one of the cooling blocks 13 as the first and second carriages 19a, 19b travel between them while holding the racks 14, 15.

The aforementioned optical measuring unit 9, located on a path along which each second carriage 19b travels between the two incubators 10, examines samples of each individual well 16 in a well rack 14 which has been carried by one of the second carriages 19b.

Further, a first pusher 18a is provided at one end (left side as shown in FIG. 1) of each incubating block 12 while a second pusher 18b is provided at one end (right side as shown in FIG. 1) of each cooling block 13 in such a way that the individual pushers 18a, 18b would not go into contact with either the first carriages 19a or the second carriages 19b. The first and second pushers 18a, 18b push the individual racks 14, 15 which have been brought by the first and second carriages 19a, 19b, respectively, so that the racks 14, 15 move between the adjacent guide members 17.

Heat-insulating partitions 24 are provided below the individual guide members 17 mentioned above as shown in FIG. 6. The heat-insulating partitions 24 act to thermally isolate the incubating blocks 12 and the cooling blocks 13 from one another. The cooling blocks 13 are provided with respective cooling plates 23 for cooling the racks 14, 15 while supporting them, the cooling plates 23 being located to one side of each heat-insulating partition 24. The cooling plates 23 are formed of a material having a high thermal conductivity, such as aluminum or copper plates, and designed to be cooled to a temperature as low as room temperature by heat dissipation.

On the other hand, the incubating blocks 12 are provided with respective heating plates 21 for heating the racks 14, 15 while supporting them, the heating plates 21 being located to the other side of each heat-insulating partition 24. One each cooling fan 22 is provided above the heating plates 21 to blow air onto the racks 14, 15 which are supported by the heating plates 21. The cooling fan 22 is activated when it is desired to lower the processing temperature of each incubating block 12. The aforementioned heating plates 21 are individually provided with unillustrated heaters and temperature sensors. The heaters heat the individual heating plates 21 and maintain them at specified temperatures. The temperature sensors detect the temperature of each heating plate 21 and output sensing signals to a controller which is not illustrated. The controller performs incubation of samples, for instance, at the specified temperatures by executing an analysis operation routine shown in FIG. 8, in which the processing temperature in the incubating blocks 12 is swiftly varied by moving the racks 14, 15 between each pair of the incubating block 12 and the cooling block 13 by means of the aforementioned first and second pushers 18a, 18b and the first and second carriages 19a, 19b.

Operation of the incubators 10 thus constructed is now described with reference to the flowchart of FIG. 8.

Figure 8:
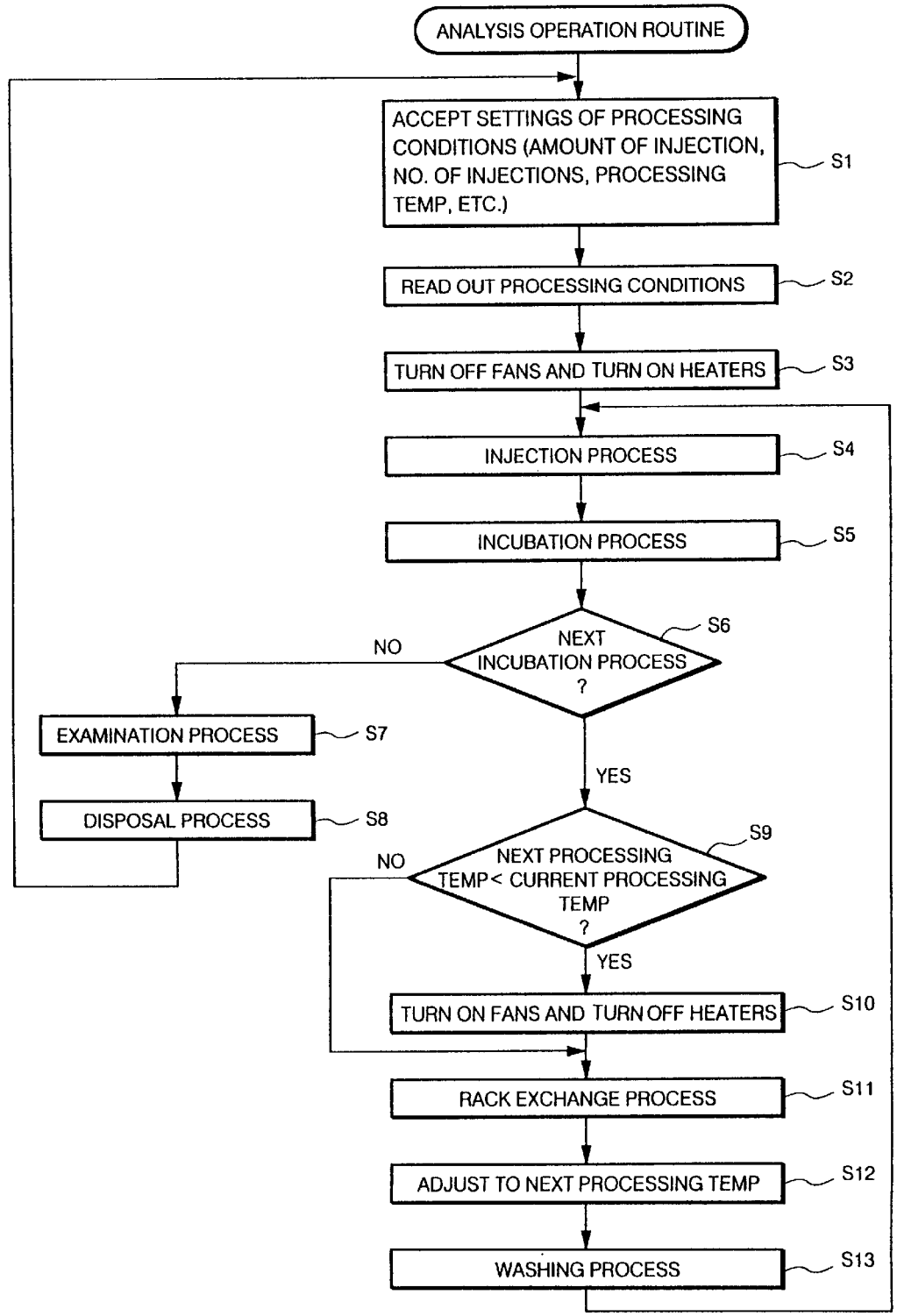
FIG. 8 is a flowchart showing an analysis operation routine carried out by the analyzer.
Figure 9:
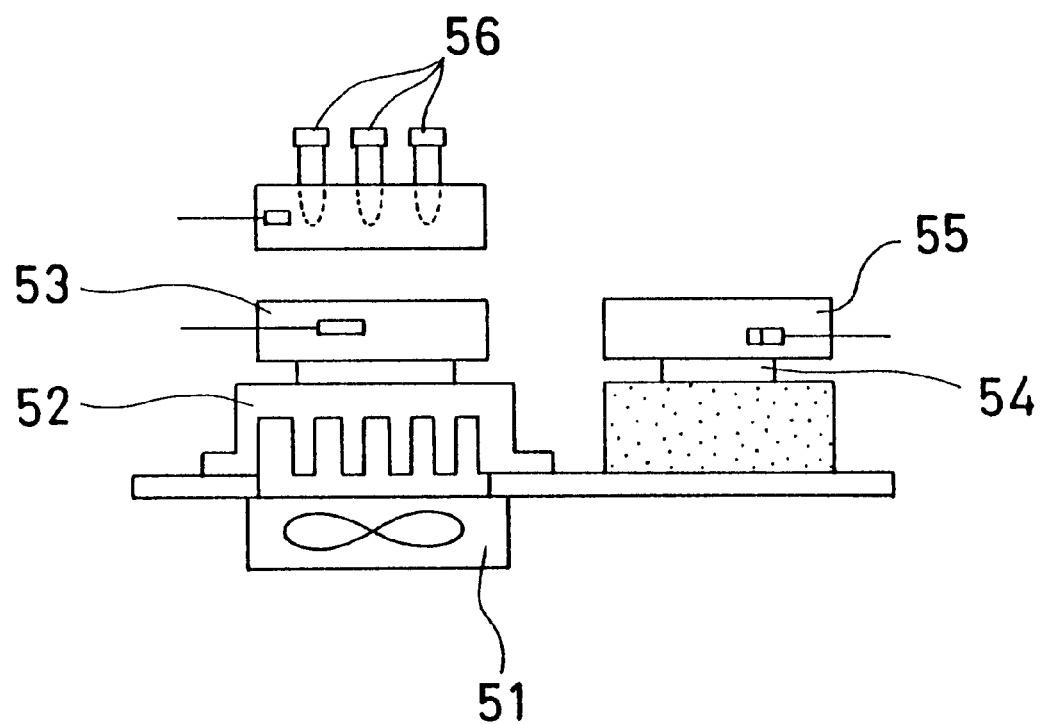
FIG. 9 is a general construction diagram of a conventional incubator.

When the unillustrated controller is powered on, it prepares itself to execute the analysis operation routine shown in FIG. 8. At this point, the controller becomes ready to accept settings of various processing conditions such as the amount of injection, the number of injections and processing temperatures (step S1). When such processing conditions entered by an operator have been stored in a memory, the processing conditions are read out from the memory (step S2). The controller causes the individual incubators 10 to be heated up to the processing temperature specified in the processing conditions by setting the cooling fans 22 of the incubators 10 to an OFF state and the heaters of the heating pkates 21 to an ON state (step S3).

After confirming that the well racks 14 are present in the cooling blocks 13 and the dummy racks 15 are present in the incubating blocks 12, the second pusher 18b of each cooling block 13 is caused to move toward the first carriage 19a at the opposite side as shown in FIG. 1, so that the well rack 14 at an extreme end is pushed against and held by the first carriage 19a. Subsequently, the first pusher 18a of each incubating block 12 is retracted and each successive well 16 is brought to one of injecting positions A by moving each first carriage 19a toward the relevant incubating block 12 in steps of the intervals between the successive wells 16. At the same time, individual samples such as specimens for instance, are brought from the storage section 3 to the relevant injecting position A by means the transport arm 5 to thereby inject the samples into the successive wells 16 at that injecting position A.

When the aforementioned well rack 14 reaches the relevant incubating block 12, one of the first carriages 19*a* is moved to that incubating block 12 and the relevant first pusher 18*a* is caused to move forward so that the dummy rack 15 positioned at an extreme end of the incubating block 12 is pushed against and held by one of the second carriages 19*b*.

Then, the second pusher 18*b* is retracted and the second carriage 19*b* is moved toward the relevant cooling block 13 to thereby transfer the dummy rack 15 to the cooling block 13, where an injection process for one well rack 14 is completed (step S4).

When the injection process for all the well racks 14 has been completed in the above-described manner, they are all located in the incubating blocks 12 while all the dummy racks 15 are located in the cooling blocks 13. The well racks 14 are then maintained at the processing temperature reached in step S3 to thereby perform an incubation process (step S5). Subsequently, when the incubation process finishes after a specified period of time has elapsed, it is judged whether to carry out a succeeding incubation process at any subsequent processing temperature setting (step S6). If it is not necessary to perform a further incubation process (No in step S6), a reagent, for instance, is injected into the wells 16 of each well rack 14 by the same incubation process as described above and, then, an examination process is carried out.

Figure 2:
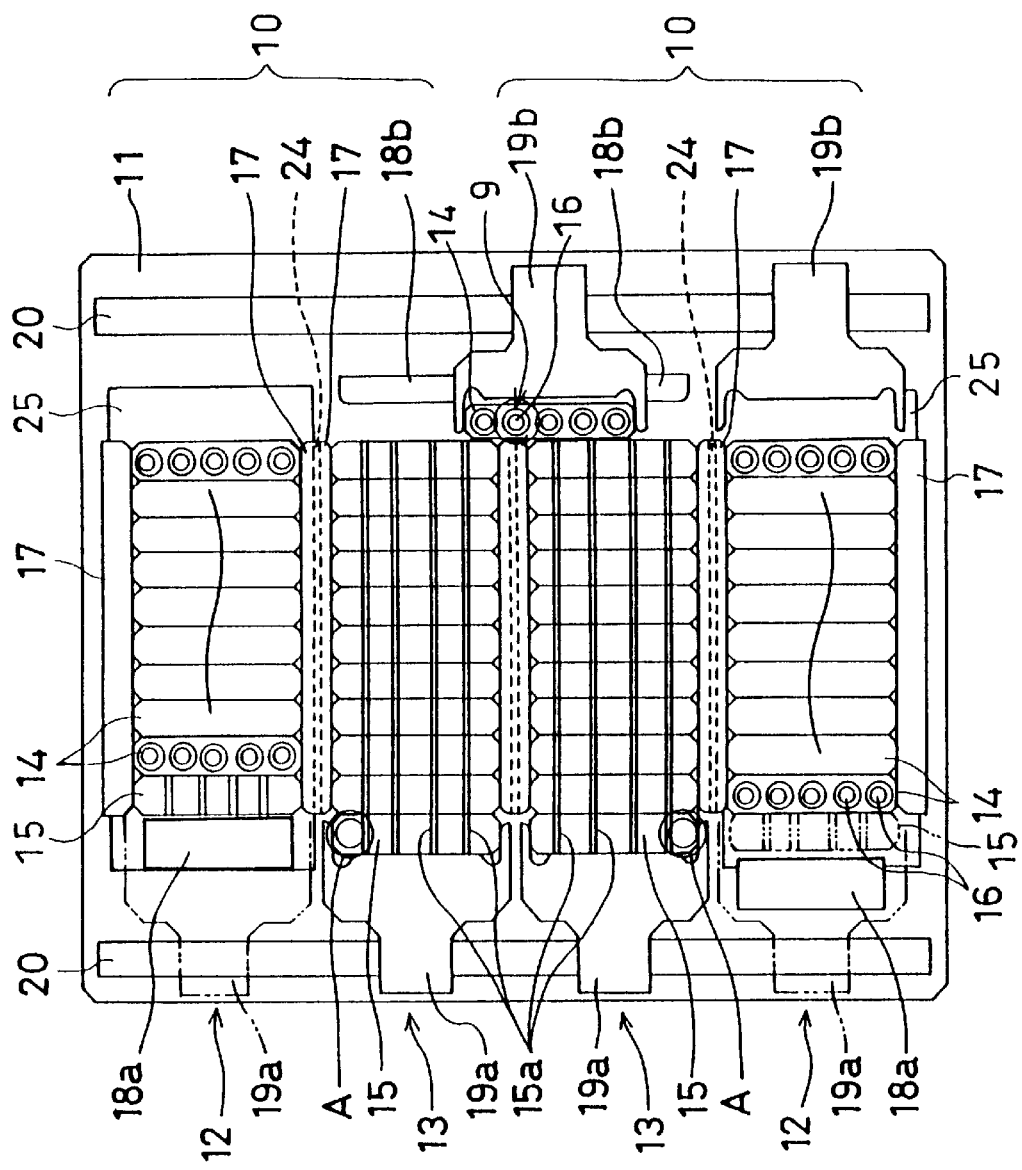
FIG. 2 is also a plan view of the incubators.

Specifically, a well rack 14 positioned in one incubating block 12 is pushed by the relevant first pusher 18*a* toward the corresponding second carriage 19*b*, causing the second carriage 19*b* to hold the well rack 14, and the second carriage 19*b* is moved together with the well rack 14 toward the optical measuring unit 9, as shown in FIG. 2. The second carriage 19*b* is stopped when the well 16 at an extreme end position of the well rack 14, opposite to its moving direction, reaches a position below the optical measuring unit 9. The light-shielding hood 33 is then caused to descend and cover up the well 16 so that the well 16 is kept in a darkroom environment as shown in FIG. 7. Next, the optical guide tube 31 which has been closed off by the shutter plate 32 is switched from a closed state to an open state to permit light from the sample reacted with the reagent, for instance, to enter the interior of the photomultiplier module 30 through the optical guide tube 31. The condition of the sample is examined based on an output signal caused by the incident light detected by the photomultiplier module 30.

When one examination process has finished in the above-described manner, the optical guide tube 31 is switched to its closed state by the shutter plate 32 and the light-shielding hood 33 is caused to ascend. Then, the second carriage 19*b* moves the well rack 14 toward the relevant incubating block 12 as much as the interval between the successive wells 16 in preparation for examination of the sample in the adjacent well 16, and the sample is examined in the same way as described above. When the samples in the wells 16 of the well rack 14 have been examined by the aforementioned sequence of processing steps, the well rack 14 is advanced to the relevant cooling block 13 and the succeeding well rack 14, which has not been subjected to examination is picked up from the incubating block 12 and carried to the optical measuring unit 9 as shown in FIG. 2. The reason why the examination process is performed while moving each well rack 14 toward the relevant incubating block 12 is that the time required from injection to examination can be equal-ized for all the wells 16 by moving each well rack 14 in the same direction as in the injection process at the injecting position A (step S7). Subsequently, A disposing process of the samples as carried out (step S8), and thereafter the analyzer waits for a succeeding entry of processing conditions by re-executing the aforementioned step S1.

On the other hand, if it is necessary to perform a further incubation process (Yes in step S6), a judgment is made as to whether the succeeding processing temperature is lower than the current processing temperature (step S9). If the succeeding processing temperature is lower than the current processing temperature (Yes in step S9), the cooling fans 22 are switched to an ON state and the heaters are switched to an OFF state (step S10). All the dummy racks 15 are moved to the incubating blocks 12 while all the well racks 14 are moved to the coolling blocks 13 by repeatedly performing rack exchange operation, in which the dummy racks 15 in the individual cooling blocks 13 are successively carried to their corresponding incubating blocks 12 by the respective first carriages 19*a* while the well racks 14 in the individual incubating blocks 12 are successively carried to their corresponding cooling racks 13 by the respective second carriages 19*b*. The whole dummy racks 15 are moved to the incubating blocks 12 while the whole well racks 14 are moved to the cooling blocks 13 in this way. As a consequence, the temperature of the heating plates 21 quickly drops because the dummy racks 15 which have been cooled in the cooling blocks 13 cool the individual heating plates 21 while the cooling fans 22 accelerate heat dissipation by blowing air against the heating plates 21 (step S11).

When the temperature of the heating plates 21 has dropped almost to the next processing temperature, the cooling fans 22 are switched to the OFF state and the heaters are switched to the ON state to thereby adjust the heating plates 21 to the intended processing temperature (step S12) and unwanted chemicals, for instance, are removed by performing a washing process (step S13). All the well racks 14 are brought to the incubating blocks 12 while all the dummy racks 15 are brought to the incubating blocks 12 by performing the injection process of step S4 and, then, the incubation process is re-executed. As a consequence, the intended next processing temperature is promptly reached even when there is a large difference between the current processing temperature and the next processing temperature, and this makes it possible to commence the succeeding incubation process after a short waiting time.

On the other hand, if the next processing temperature is not lower than the current processing temperature (No in step S9), all the dummy racks 15 are moved to the incubating blocks 12 while all the well racks 14 are moved to the cooling blocks 13 by repeatedly performing the rack exchange operation (step S11). After adjusting the incubating blocks 12 to the next processing temperature by heating them by the respective heaters (step S12), unwanted chemicals, for instance, are removed by performing the washing process (step S13). Subsequently, the injection process of step S4 is performed, and then the incubation process is re-executed. Since the incubating blocks 12 are so constructed that the rate of heat dissipation is reduced, their temperature swiftly increases by heating of the heaters. Therefore, the intended processing temperature is promptly reached even when there is a large difference between the current processing temperature and the next processing temperature, and this makes it possible to commence the succeeding incubation process after a short waiting time.

In one feature of the above-described embodiment of the invention, each incubator 10 comprises the well racks 14 for holding samples such as specimens for instance, the incubating block 12 (incubation means) for performing the incubation process in which the well racks 14 are maintained at a desired processing temperature to incubate the samples at that processing temperature, the cooling block 13 (cooling means) which is set to a cooling temperature, the dummy racks 15 which are cooled by the cooling block 13 during the incubation process, and the first and second pushers 18a, 18b and the first and second carriages 19a, 19b (exchange means) for replacing the well racks 14 and the dummy racks 15 with one another, as shown in FIG. 1.

In this construction, when the dummy racks 15 cooled by the cooling blocks 13 are replaced with the well racks 14, the incubating blocks 12 are forcibly cooled by the dummy racks 15. Thus, a high rate of temperature drop of the incubating blocks 12 is obtained, even when the rate of heat dissipation of the incubating blocks 12 is decreased so that the temperature rise thereof can be expedited. Since both the rate of temperature rise and the rate of temperature drop can be increased, it is possible to achieve high-speed temperature control capable of swiftly following arbitrarily defined processing temperature settings.

Furthermore, since incubating operation and cooling operation for the samples in the well racks 14 can be performed independently in the incubating blocks 12 and in the cooling blocks 13 respectively, it is possible to design the individual blocks 12, 13 in such a way that each incubating block 12 has a structure suited for the incubating operation and each cooling block 13 has a structure suited for the cooling operation. Accordingly, overall design work becomes easier than designing a structure suited for the incubating and cooling operation.

Furthermore, the dummy racks 15 are cooled in the cooling blocks 13 during the well racks 14 are incubated in the incubating blocks 12, while on the other hand, the well racks 14 are cooled in the cooling blocks 13 during the incubating blocks 12 are cooled by the dummy racks 15. Accordingly, it is possible to efficiently perform the incubating and cooling operations without requiring such meaningless operations as temporarily moving the dummy racks 15 or the well racks 14 to locations other than the incubating blocks 12 and the cooling blocks 13.

In another feature of the present embodiment, each incubator 10 comprises a well 16 for holding a sample, a plurality of well racks 14 which accommodate the well and are arranged parallel to one another, the incubating block 12 (incubation means) for performing the incubation process in which the well racks 14 are maintained at a desired processing temperature to incubate the samples at that processing temperature, the cooling block 13 (cooling means) which is set to a specific cooling temperature, a plurality of dummy racks 15 which are cooled by the cooling block 13 during the incubation process and arranged parallel to one another, the transport arm 5 (injection means) which is disposed at one injecting position A located between the incubating block 12 and the cooling block 13 and inject the samples and the reagent into the wells 16 of each well rack 14 passing through the injecting position A, and the first and second pushers 18a, 18b and the first and second carriages 19a, 19b (exchange means) which together replace the well racks 14 and the dummy racks 15 with one another between the incubating block 12 and the cooling block 13 by moving the individual well racks 14 and dummy racks 15 so that they pass through the injecting position A.

This construction makes it possible to efficiently incubate and cool the multiple well racks 14. Furthermore, it is possible to efficiently perform sample injecting operation for the individual well racks 14 as the sample can be injected into the well of each well rack 14 on its way from the cooling block 13 to the incubating block 12 by means of the transport arm 5.

The incubating blocks 12 are equipped with their respective cooling fans 22 which are activated when reducing the processing temperature in the construction of this embodiment. This makes it possible to further increase the rate of temperature drop of the incubating blocks 12.

While the cooling plates 23 of the cooling blocks 13 of this embodiment are formed of a material having a high thermal conductivity and designed to be cooled to a temperature as low as room temperature, the cooling blocks 13 are not limited to this construction. Alternatively, cooling acceleration means, such as a cooling device like a Peltier element, a cooling fan or a radiator, for instance, may be attached to each cooling plate 23 so that it can be cooled at a high cooling efficiency, making it possible to set a cooling temperature lower than room temperature. In this alternative construction, the dummy racks 15 can be instantly cooled when the dummy racks 15 which have been heated in the incubating blocks 12 are returned to the cooling blocks 13 and, therefore, it becomes possible to follow the set processing temperature at an even higher speed.

In still another feature of the embodiment, there are formed the grooves 15a in the dummy racks 15 to increase their surface areas to thereby accelerate heat dissipation. As the increased surface areas accelerate heat dissipation in this construction, it is possible to promptly cool the individual dummy racks 15. Although the grooves 15a are formed widthwise across the individual dummy racks 15 in this embodiment, the grooves 15a may be formed lengthwise along the dummy racks 15, or both widthwise and lengthwise.

In yet another feature of the embodiment, the incubating blocks 12 and the cooling blocks 13 which are arranged parallel to one another accommodate a plurality of well racks 14 and dummy racks 15 parallel to one another in a manner that the individual racks 14, 15 can be moved in one direction, and the exchange means for replacing the well racks 14 and the dummy racks 15 one another is constructed as follows. Specifically, the exchange means of each incubator 10 includes the first pusher 18a which is provided at one end (left side as illustrated) of the incubating block 12 and can push the racks 14, 15 accommodated in the incubating block 12 toward its opposite end, the second pusher 18b which is provided at one end (right side as illustrated) of the cooling block 13 and can push the racks 14, 15 accommodated in the cooling block 13 toward its opposite end, and the first and second carriages 19a, 19b which are provided at both ends of the incubating block 12 and the cooling block 13 and can hold the racks 14, 15 pushed out by the first and second pushers 18a, 18b, the first and second carriages 19a, 19b being made movable in a direction along which the incubating block 12 and the cooling block 13 are arranged.

Since the exchange means is constructed of such simple mechanical components as the first and second pushers 18a, 18b and the first and second carriages 19a, 19b, it is possible to reduce component costs of the individual incubating blocks 12 as well as manufacturing costs incurred in their assembly operation.

In the aforementioned construction of the embodiment, the optical measuring unit 9 (examination means) is shared by one pair of the incubators 10. As the optical measuring unit 9, whose cost tends to increase dramatically due to a move toward higher accuracy of analysis, is shared by the two incubators 10, it is possible to reduce the component costs. It is to be noted that there may be provided more than two incubators 10.

In a further feature of the embodiment, the optical measuring unit 9 (examination means) is located on the path along which the second carriages 19b of the individual incubators 10 travel. Since each well rack 14 can be moved by one of the second carriages 19b up to the location of the optical measuring unit 9 and subjected to an examination in this construction, it is possible to achieve a further reduction in component costs.

Although the foregoing discussion has revealed that the optical measuring unit 9 is immovably provided between the two incubators 10 in this embodiment, the invention is not limited to this construction. In one varied construction, the optical measuring unit 9 (examination means) may be provided on the transport arm 5 which can move to a any desired position over the incubators 10 so that the samples are carried to and from the well racks 14 on the incubators 10.

Since the optical measuring unit 9 can be moved to and set in a any desired position over the incubators 10 by the transport arm 5 in this construction, the optical measuring unit 9 can always be shared by the incubators 10 regardless of the direction in which the incubators 10 are arranged or the number of the incubators 10. Accordingly, it becomes possible to increase the degree of freedom in designing an analyzer with respect to its technical specifications, such as equipment layout and the scale of examination. As the transport arm 5 for moving the optical measuring unit 9 is originally intended for carrying the samples to and from the well racks 14, this construction does not entail an increase in component costs as would be incurred when a dedicated mechanism for moving the optical measuring unit 9 is provided.

INDUSTRIAL APPLICABILITY

The present invention is advantageous if it is implemented in such apparatus as Nucleic acid automation analyzers or blood analyzers, in which it is necessary to perform various kinds of processing on samples at optimum processing temperatures. The invention is particularly suited to those apparatus which are required to control the temperature following any processing temperature settings at a high speed.

What is claimed is:

1. An incubator comprising:

a vessel for holding a sample;

a well rack for accommodating said vessel;

incubation means for incubating said sample at an any desired processing temperature by storing said well rack under that temperature;

cooling means set to a cooling temperature; a dummy rack being cooled by said cooling means during said sample incubation; and exchange means for exchanging said well rack and said dummy rack with each other between said incubation means and said cooling means.

2. An incubator comprising:

a vessel for holding a sample;

a plurality of well racks for accommodating said vessel, being arranged parallel to one another;

incubation means for incubating said sample at an any desired processing temperature by storing said well racks under that temperature;

cooling means set to a cooling temperature;

a plurality of dummy racks being cooled by said cooling means during said sample incubation, and said dummy racks being, arranged parallel to one another and;

injection means, settled at an injecting position set between said incubation means and said cooling means, for injecting the sample into said well of said well racks passing the injecting position; and exchange means for exchanging said well racks and said dummy racks with one another between said incubation means and said cooling means by transporting said well racks and said dummy racks through the injecting position.

3. An incubator according to claim 1, wherein said incubation means includes a cooling fan which is operated when lowering the processing temperature.

4. An incubator according to claim 1, wherein said cooling means includes cooling acceleration means for accelerating cooling operation.

5. An incubator according to wherein a groove for accelerating heat dissipation by increase of its surface area is formed in said dummy rack.

6. An incubator according to claim 1, wherein said incubation means and said cooling means individually store a plurality of said well racks and said dummy racks parallel to one another in such a way that they can be moved in one direction, said incubation means and said cooling means being arranged parallel to each other;

and wherein said exchange means includes:

a first pusher, provided at one end of said incubation means, being capable of pushing out any one of said well racks and said dummy racks stored in said incubation means to its other end;

a second pusher, provided at one end of said cooling means, opposite to the end of said incubation means where said first pusher is provided, said second pusher being capable of pushing out any one of said well racks and said dummy racks accommodated in said cooling means to its other end; and carriages provided at both ends of said incubation means and said cooling means in such a way that said carriages can move in a direction along which said incubation means and said cooling means are arranged, said carriages being capable of holding any one of said well racks and said dummy racks pushed out by said first pusher and said second pusher.

7. An analyzer comprising a plurality of incubators according claim 1 and examination means for examining samples of said well racks stored in said incubators, said examination means is shared by said incubators.

8. An analyzer according to claim 7, which further includes a transport means capable of moving to an any desired position over said incubators so that it can carry the samples to and from said well racks, said examination means is attached to said transport means.

9. An analyzer comprising a pair of incubators according to claim 6 and examination means for examining samples of well racks stored in said incubators, said examination means is located on a path along which each of said carriages travels between said incubators.

* * * * *